US012697498B2

(12) United States Patent
Anderson et al.

(10) Patent No.: US 12,697,498 B2
(45) Date of Patent: Aug. 4, 2026

(54) USING WIRELESS POWER TRANSFER COILS FOR INDUCTIVE TELEMETRY

(71) Applicant: TC1 LLC, St. Paul, MN (US)

(72) Inventors: Russell Eugene Anderson, Hopkins, MN (US); Pritika Toutam, Hennepin, MN (US); Manoj Rahel, Billerica, MA (US); Brian David Kimball, Medford, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 18/730,183

(22) PCT Filed: Jan. 20, 2023

(86) PCT No.: PCT/US2023/060956
§ 371 (c)(1),
(2) Date: Jul. 18, 2024

(87) PCT Pub. No.: WO2023/141546
PCT Pub. Date: Jul. 27, 2023

(65) Prior Publication Data
US 2025/0144432 A1 May 8, 2025

Related U.S. Application Data

(60) Provisional application No. 63/301,638, filed on Jan. 21, 2022.

(51) Int. Cl.
*A61N 1/378* (2006.01)
*A61N 1/372* (2006.01)
(Continued)

(52) U.S. Cl.
CPC ....... *A61N 1/3787* (2013.01); *A61N 1/37223* (2013.01); *G08C 17/04* (2013.01); *H04B 5/266* (2024.01); *H02J 50/12* (2016.02)

(58) Field of Classification Search
CPC .. A61N 1/3787; A61N 1/37223; G08C 17/04; H04B 5/266; H04B 5/24; H04B 5/79; H02J 50/12; H02J 50/80
See application file for complete search history.

(56) References Cited

U.S. PATENT DOCUMENTS 5,713,939 A * 2/1998 Nedungadi ........ A61N 1/37211
607/33
10,716,945 B2 * 7/2020 Baumgartner .......... H02J 50/90
(Continued)

OTHER PUBLICATIONS

PCT International Search Report and Written Opinion, Application No. PCT/US2023/060956, dated Mar. 31, 2023, 15 pages.
(Continued)

*Primary Examiner* — Amine Benlagsir
(74) *Attorney, Agent, or Firm* — Armstrong Teasdale

(57) ABSTRACT

The present disclosure generally relates to wireless power transfer systems, and more specifically, relates to using a wireless power system for inductive telemetry communications. Accordingly, the present disclosure describes providing an inductive telemetry control signal to the wireless power coils associated with a transcutaneous energy transfer system to generate a telemetry communication signal. The transcutaneous energy transfer system includes a wireless power transfer transmit coil and a wireless power transfer receive coil. The telemetry communication signal may be transmitted from the wireless power transfer receive coil to the wireless power transfer transmit coil, as well as from the wireless power transfer transmit coil to the wireless power transfer receive coil for bidirectional communication.

20 Claims, 8 Drawing Sheets

(51) Int. Cl.
    *G08C 17/04*       (2006.01)
    *H04B 5/26*        (2024.01)
    *H02J 50/12*       (2016.01)

(56)            References Cited

U.S. PATENT DOCUMENTS

2018/0126053 A1*   5/2018   Zilbershlag ......... A61M 60/216
2021/0267523 A1*   9/2021   Donoghue ........... A61N 1/0529
2021/0360353 A1*   11/2021   Croghan .............. H04R 25/356

OTHER PUBLICATIONS

Mohammad Javad Karimi et al., "Wireless Power and Data Transmission for Implanted Devices via Inductive Links: A Systematic Review", IEEE Sensors Journal, vol. 21, No. 6, Mar. 15, 2021, pp. 7145-7161.

* cited by examiner

USING WIRELESS POWER TRANSFER COILS FOR INDUCTIVE TELEMETRY

CROSS REFERENCE TO RELATED APPLICATIONS

This application is a National Stage application of PCT Application Serial No. PCT/US2023/060956, filed Jan. 20, 2023, which claims priority to U.S. Provisional Patent Application No. 63/301,638, filed Jan. 21, 2022, both of which are incorporated herein by reference in their entirety.

BACKGROUND OF THE DISCLOSURE

Field of the Disclosure

The present disclosure generally relates to wireless power transfer systems, and more specifically, relates to using a wireless power system for inductive telemetry communications.

Background

A transcutaneous energy transfer system typically uses two inductive coils to perform a wireless power transfer process. For example, a transmit coil may be placed at a first location and a receive coil may be placed at a second location. In a medical device application, the transmit coil is typically placed outside of the body while the receive coil, along with at least a portion of the medical device, is implanted in the body. The implanted portion of the medical device is powered by the transcutaneous energy transfer system.

SUMMARY OF THE DISCLOSURE

The present application describes a method for using wireless power transfer coils of a transcutaneous energy transfer system to enable wireless communication between different components of a system. The method includes providing a telemetry control signal (e.g., a step voltage) to transmit circuitry of a controller associated with a transcutaneous energy transfer system to generate a telemetry communication signal. In an example, the transcutaneous energy transfer system includes a wireless power transfer transmit coil and a wireless power transfer receive coil. The method also includes transmitting the telemetry communication signal from the wireless power transfer receive coil to the wireless power transfer transmit coil.

The present application also describes a transcutaneous energy transfer system for an implantable device. The transcutaneous energy transfer system includes a wireless power transfer transmit coil, a wireless power transfer receive coil and a controller. The controller is associated with the wireless power transfer receive coil. In an example, the controller includes transmit circuitry and receive circuitry. As will be explained in greater detail below, the transmit circuitry and the receive circuitry enable bi-directional communication via the coils. A telemetry communication signal is generated in response to receipt of a voltage. The telemetry communication signal is transmitted to the wireless power transfer transmit coil from the wireless power transfer receive coil via the transmit circuitry.

Also described is a method for using wireless power transfer coils of a transcutaneous energy transfer system to enable wireless communication between different components of a system. This method includes detecting an operating state of a communication system associated with an implantable device. In an example, the implantable device includes a transcutaneous energy transfer system. The transcutaneous energy transfer system includes a wireless power transfer transmit coil and a wireless power transfer receive coil. A telemetry control signal is provided to transmit circuitry of the controller to generate a telemetry communication signal in response to detecting an operating state of the communication system. The telemetry communication signal is then transmitted from the wireless power transfer receive coil to the wireless power transfer transmit coil.

DETAILED DESCRIPTION OF THE DISCLOSURE

Figure 1:
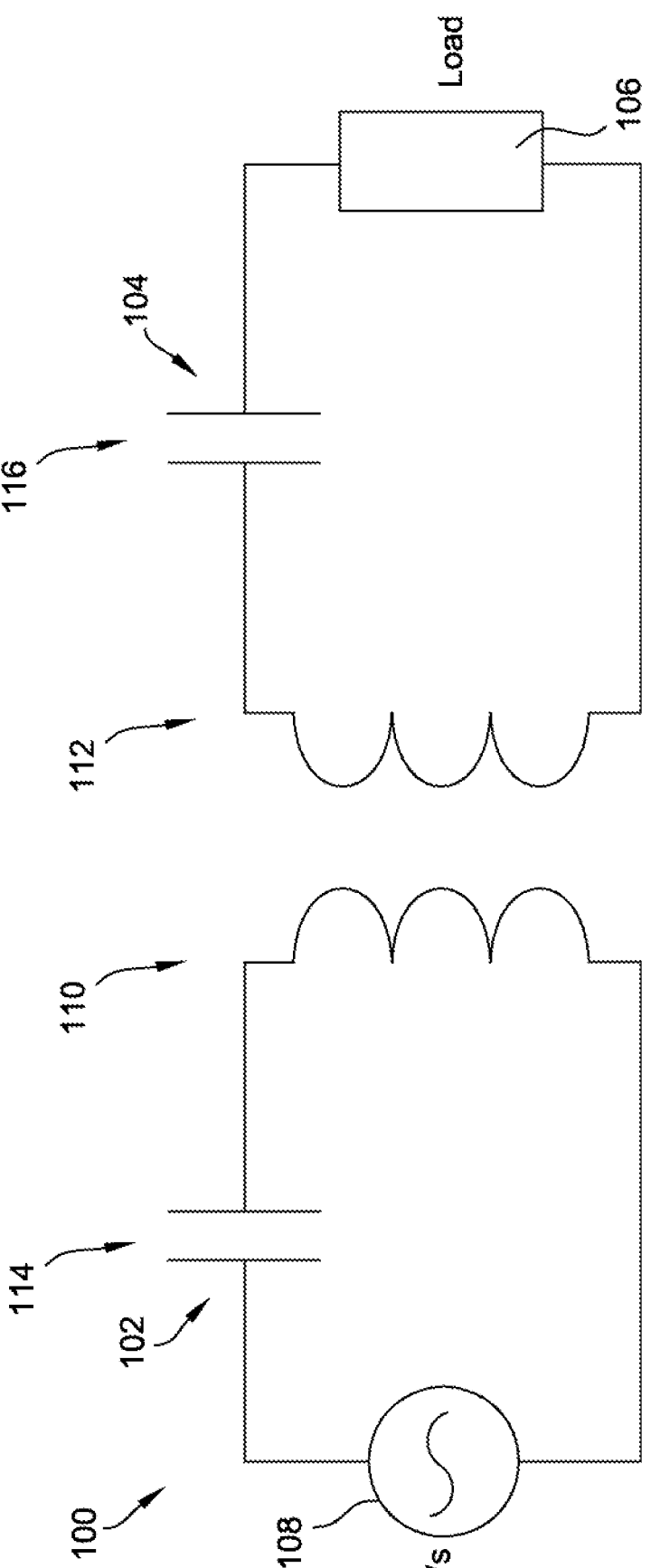
FIG. 1 is a simplified electrical circuit diagram of a wireless power transfer system according to an example.

The present disclosure generally relates to wireless power transfer systems, and more specifically, relates to using a wireless power system for inductive telemetry communications. For example, the present disclosure describes how wireless power transfer coils of a transcutaneous energy transfer system may be used to transmit bi-directional inductive telemetry communications. The bi-directional inductive telemetry communications may be used as a primary form of communication between, for example, an implantable device and a monitoring system. In another example the bi-directional inductive telemetry communications may be used as back-up or a failover communication method should another communication system (e.g., a Bluetooth low energy communication system) fail.

An implantable medical device may receive power from, or otherwise be powered by, a wireless power transfer system. The wireless power transfer system uses inductive coils to enable the wireless power transfer. In transcutaneous energy transfer systems, in which power is transferred over a distance, highly resonant structures are used. The resonant structures include an inductive coil that is matched with a capacitive element to operate in a state of resonance. This resonant state allows for a very efficient transfer of power when each of the coils in the system share the same resonant frequency.

Although a highly resonant design is desirable for transferring energy in a transcutaneous energy transfer system, the same coil structures are not typically used for a telemetry or communication scheme. For example, in a medical device application (e.g., when at least a portion of a medical device is implanted in an individual), communication between the various components of the medical device is via a Bluetooth Low Energy communication channel or other wireless form of communication. The communication between the various components of the medical device may include information about the status of the implantable medical device including, but not limited to, an alarm regarding a state of a pump or other component of the implantable medical device, a battery status of the implantable medical device, or other critical parameters associated with the implantable medical device.

However, having a single communication pathway can be problematic. For example, if the single communication pathway is down or malfunctions, there is no way to notify the individual about the operating state of the implantable medical device.

Accordingly, the present application describes using resonant structures that are used for wireless power transfer as a way to generate and/or provide inductive telemetry communications between the implantable medical device and a monitoring system or other medical device. Having an additional communication channel may help increase the safety and reliability of the system. Although a medical device is specifically mentioned, the examples described herein may be used in a number of different devices. Additionally, the examples described herein may be used as a primary communication channel (e.g., in place of a Bluetooth, infrared or other communication channel) or as a back-up communication channel.

In an example, the transcutaneous energy transfer system includes an external transmit resonator and an implantable receive resonator. One or more of the resonators may be implanted inside a body of an individual. In examples, the inductive telemetry communication signal is generated and transmitted using the same resonant coil structures as the wireless power transfer process of the transcutaneous energy transfer system. For example, the telemetry communication signal may be transmitted from the external transmit resonator to the implantable receive resonator, as well as from the implantable receive resonator to the external transmit resonator for bidirectional communication. This telemetry communication signal may be generated and/or transmitted during a wireless power transfer process or in lieu of a wireless power transfer process.

For example, when the transcutaneous energy transfer system is not performing a wireless power transfer process, the resonant coil structures may be driven (e.g., by a step voltage) to generate an inductive telemetry communication signal. This signal is transmitted between the resonant coil structures. As will be explained below, each of the resonant coil structures may be configured to generate, transmit, and/or receive an inductive telemetry communication signal. As such, the communication may be bi-directional. Additionally, because the same resonant coil structures are used for the wireless power transfer process and for the bi-directional communication, there is no need for additional telemetry coils and/or matching network specifics for a particular communication channel.

The transcutaneous energy transfer system may switch between performing a wireless power transfer process and a communication process based on a number of factors. For example, an operating state of the implantable medical device may be used to determine when the coils are to transfer power and when the inductive telemetry communication signal is to be transmitted/received. In another example, the operating state of the implantable medical device may indicate that a primary communication channel associated with the implantable medical device has failed. In yet another example, the operating state of the implantable medical device may be an indication as to whether the implantable medical device is currently receiving power or whether the implantable medical device needs power. Although specific examples are given, other operating states are contemplated.

Depending on the operating state of the implantable medical device, a controller or other computing device may cause the transcutaneous energy transfer system to perform the wireless power transfer process or generate and transmit an inductive telemetry communication signal. For example, if the implantable medical device has sufficient power or is not currently receiving power via a wireless power transfer process, the controller may cause the generation and transmission of an inductive telemetry communication signal. In this example, the telemetry communication signal may be transmitted at the same frequency as used for the wireless power transfer.

The generation and transmission of the inductive telemetry communication signal may be in response to a determination that a primary communication channel associated with the implantable medical device is not operating. In another example, the generation and transmission of the inductive telemetry communication signal may be the primary communication channel between the implantable medical device and a monitoring device. In yet another example, the inductive telemetry communication signal may be generated and transmitted during a wireless power transfer process. In this example, the wireless power transfer process may occur at a first frequency while the inductive telemetry communication may occur at a second frequency. The second frequency may be a harmonic frequency (or a different frequency) of the first frequency.

As will be explained below, existing transmit and receive component structures (e.g., a wireless power transfer receive coil and/or a wireless power transfer transmit coil) are used for the generation and/or transmission of the telemetry communication signal. In an example, the telemetry scheme may utilize a pulse position modulation. The amplitude and length of the individual ping or ringing response will be highly detectable.

These and other examples will be shown and described in greater detail with respect to FIG. 1-FIG. 7.

Referring now to the drawings, FIG. 1 illustrates a simplified circuit of a wireless power transfer system 100 according to an example. The various components of the wireless power transfer system 100 may be used to transfer power and may also be used to generate and/or transmit an inductive telemetry communication signal.

The wireless power transfer system 100 includes an external transmit resonator 102 and an implantable receive resonator 104. In the system shown in FIG. 1, a power source Vs 108 is electrically connected with the transmit resonator 102 thereby providing power to the transmit resonator 102. The receive resonator 104 is connected to a load 106 (e.g., an implantable medical device). The receive resonator 104 and the load 106 may be electrically connected with a switching or rectifying device (not shown).

In an example, the transmit resonator 102 includes an inductive element or coil 110 connected to the power source Vs 108 by a capacitive element 114. Further, the receive resonator 104 includes an indicative element, or coil 112 connected to the load 106 by a capacitive element 116. The inductive elements, or coils 110, 112, may be coupled by a coupling coefficient.

In operation, the transmit resonator 102 transmits wireless power received from the power source Vs 108. Receive resonator 104 receives the power wirelessly transmitted by transmit resonator 102 and transmits the received power to load 106.

Figure 2:
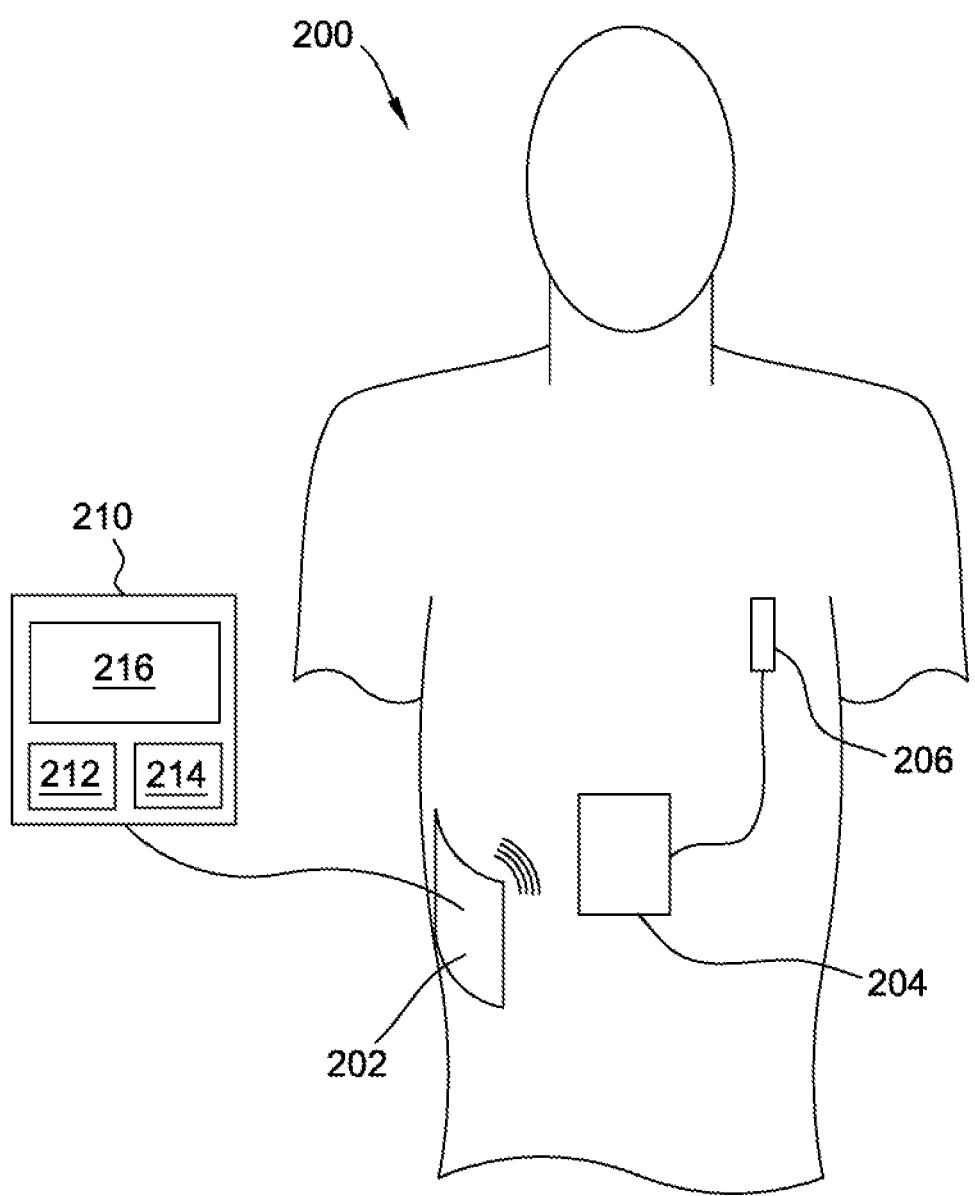
FIG. 2 is an illustration of the wireless power transfer system of FIG. 1 used to supply power to an implantable device according to an example.

FIG. 2 illustrates an example of an individual using an external coil 202 (e.g., a transmit resonator 102 (FIG. 1)) to wirelessly transmit power to an implanted coil 204 (e.g., a receive resonator 104 (FIG. 1)). Implanted coil 204 uses the received power to power an implantable device 206. For example, implantable device 206 may include a pacemaker or heart pump. In some examples, implanted coil 204 and/or implantable device 206 may include or be coupled to a battery.

In one example, external coil 202 is communicatively coupled to a computing device 210, for example, via wired or wireless connection, such that the external coil 202 may receive signals from and transmit signals to the computing device 210. The computing device 210 may be any suitable computing device including, but not limited to, desktop computers, tablet computers, wearable electronic devices, gaming systems and the like.

In some examples, the computing device 210 is a power source for the external coil 202. In other examples, the external coil 202 is coupled to an alternative power supply (not shown). The computing device 210 includes a processor 212 in communication with a memory 214. In some examples, executable instructions are stored in the memory 214.

The computing device 210 and its associated processor 212 may be used to determine or detect an operating state of the implantable device 206 and/or a communication system associated with the implantable device 206. For example, if the implantable device 206 communicates with the computing device 210 via a wireless communication channel (e.g., Bluetooth), the computing device 210 may be able to monitor the status of that communication channel. Additionally, the computing device 210 may be able to monitor or otherwise determine whether power is currently being exchanged or will be exchanged between via the transmit coil 202 and the implanted coil 204. The computing device 210 may also determine a frequency of the power transmission and/or identify one or more harmonics of the frequency. As will be explained in more detail below, an inductive telemetry communication signal may be transmitted between the transmit coil 202 and the implanted coil 204 at the same frequency of the power transmission or at a harmonic of the frequency. In the later example, the telemetry communication signal may be transmitted at the same time that power is transmitted between the transmit coil 202 and the implanted coil 204.

The computing device 210 may include a user interface (UI) 216. The UI 216 presents information to a user (e.g., the patient 200). For example, the UI 216 may include a display adapter that may be coupled to a display device, such as a cathode ray tube (CRT), a liquid crystal display (LCD), an organic LED (OLED) display, and/or an electronic ink display. In some examples, the UI 216 includes one or more display devices. Further, in some examples, the UI may be or otherwise include a presentation interface.

The presentation interface may generate visual content, audible content, and/or computer-generated spoken-word content. In an example, the UI 216 displays one or more representations designed to aid the individual 200 in placing the external coil 202 such that the coupling between the external coil 202 and the implanted coil 204 is optimal. In another example, the UI 216 may display status information and/or an operating state of the implantable device 206. In yet another example, the user UI 216 may display a received waveform (e.g., waveform 600 (FIG. 6) that was transmitted and/or received as part of the inductive telemetry communication signal. In some examples, the UI 216 may show visual information (e.g., status information) represented by the waveform once the waveform has been processed by the processor 212 of the computing device 210.

Figure 3:
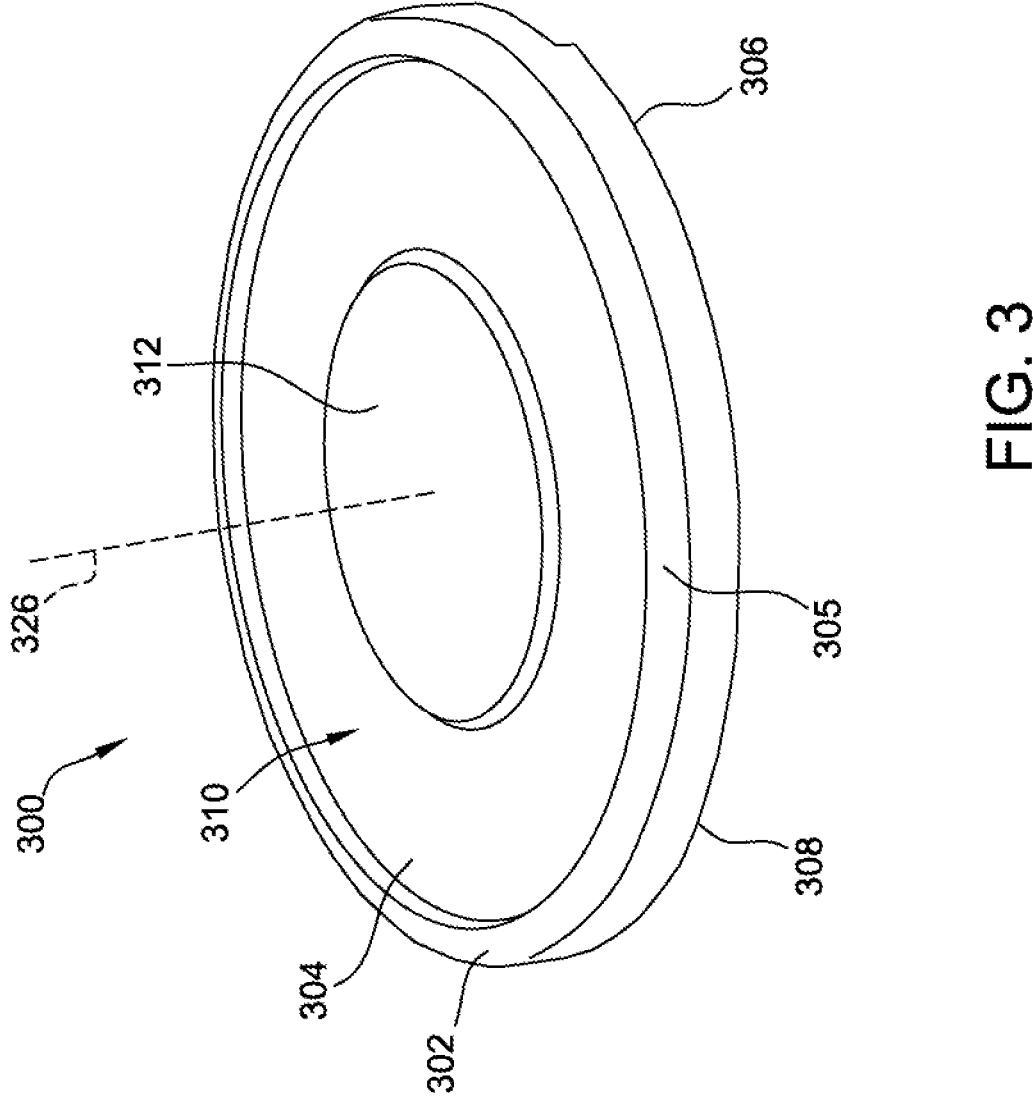
FIG. 3 is a front perspective view of on example of a resonator that may be used to implement the system shown in FIG. 1 according to an example.

FIG. 3 is a front perspective view of one example of a resonator 300 that may be used to implement the system 100 shown in FIG. 1. For example, the resonator 300 may be used to implement the external transmit resonator 102 (FIG. 1), the implantable receive resonator 104 (FIG. 1), the external coil 202 (FIG. 2), and/or the implanted coil 204 (FIG. 2).

In an example, the resonator 300 includes a core 302 and a coil element 304. The core 302 includes a front surface 305, a back surface 306, and an annular sidewall 308 extending between the front surface 305 and the back surface 306. An annular groove 310 is defined by the front surface 305 and forms a central post 312 of the core 302.

The resonator 300 (including the core 302 and the coil element 304) functions as a wireless power resonator when coupled to a capacitor (e.g., a capacitor on a printed circuit board electrically coupled to coil element 304). However, those of skill in the art will appreciate that resonator 300, without connection to a capacitor, constitutes a coil assembly. Accordingly, as used herein, the term resonator does not require that the device be coupled to a capacitor to form a wireless power resonator. In contrast, as used herein, the term resonator is broad enough to cover a coil assembly that includes a core and a coil element without connection to a capacitor, as shown in FIG. 3.

In an example, the core 302 is formed of a magnetic material. The magnetic material may be a ferrite material, such as nickel-based or manganese-based ferrites. Nickel-based ferrites generally have lower electrical conductivity and reduced losses, while manganese-based ferrites have a higher magnetic permeability (while still having acceptable losses), facilitating containing magnetic field lines, and reducing fringing fields entering nearby conductors (e.g., a titanium enclosure or copper in a nearby PCB) to prevent losses. In other examples, other types of ferrite materials may be used. For example, in some examples, a magnesium-based ferrite (e.g., MgCuZn, which may outperform nickel-based and manganese-based ferrites in a frequency range around 1 Megahertz (MHz)) may be used.

The coil element 304 is positioned within the annular groove 310 and surrounds the central post 312. The resonator 300 may be, for example, a Litz wire resonator or a stacked plate resonator. In a Litz wire resonator, the coil element 304 includes a plurality of loops of Litz wire. In a stacked plate resonator, the coil element 304 includes a plurality of stacked plates that may include a plurality of alternating dielectric layers and conductive layers arranged in a stack. The dielectric layers may be formed of, for example, ceramic, plastic, glass, and/or mica.

The coil element 304 may be electrically coupled to a power source (when functioning as a transmit resonator) or a load (e.g., load 106 (FIG. 1)) when functioning as a receive resonator. In operation, when power is supplied to the resonator 300 operating as a transmit resonator, current flows through the coil element 304, creating an inductive current loop. This inductive current loop is capable of wirelessly transmitting power to a second resonator 300, provided that resonance frequencies of the first and second resonators 300 overlap. In the example shown, the coil element 304 includes a plurality of terminals 314 that extend through core 302 to the rear surface 306. Terminals 314 facilitate electrically coupling the coil element 304 to a power supply or load.

In order for the coil element 304 to transmit or otherwise generate an inductive telemetry communication signal, a telemetry control signal (e.g., a step voltage, a ramp voltage, a piecewise linear edge) may be applied to the resonator. In an example, telemetry control signal may be any voltage between approximately 0.5 volts and approximately 5 volts. Although specific voltages are mentioned, other voltages may be used. For example, the voltage may be less than 0.5 volts or greater than 5 volts. As the telemetry control signal is supplied to the resonator, a resonant voltage and an associated waveform may be transmitted between a transmit resonator and a receive resonator. In some examples, the telemetry control signal may be applied to either the transmit resonator and/or the receive resonator thereby allowing bi-directional communication between each resonator.

Figure 4:
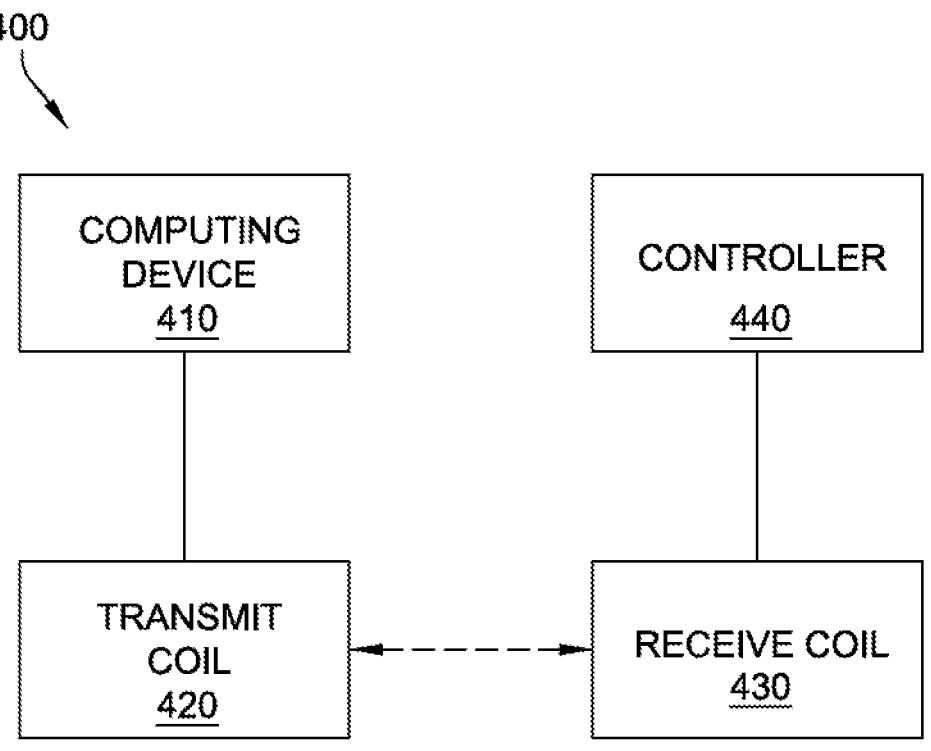
FIG. 4 illustrates an example wireless power transfer system that may be used to implement bi-directional inductive telemetry communications according to an example.

FIG. 4 illustrates an example system 400 that includes a wireless power transfer system that supports bi-directional inductive telemetry communications. As shown in FIG. 4, the system 100 includes a wireless power transfer transmit coil 420 and a wireless power transfer receive coil 430. The wireless power transfer transmit coil 420 may be similar to, or otherwise be associated with, the external transmit resonator 102 (FIG. 1) and/or the external coil 202 (FIG. 2). Likewise, the wireless power transfer receive coil 430 may be similar to, or otherwise be associated with, the implantable receive resonator 104 (FIG. 1) and/or the implanted coil 204 (FIG. 2).

The wireless power transfer transmit coil 420 may be coupled (communicatively or otherwise) to a computing device 410. The computing device 410 may be similar to the computing device 210 (FIG. 2). As shown in FIG. 4, the receive coil 430 may be coupled (communicatively or otherwise) to a controller 440. In some examples, the controller 440 may be associated with an implantable device. Accordingly, the controller 440 may be used to determine an operating status of the implantable device.

For example, the controller 440 may be configured to determine whether power is currently being transferred between the wireless power transfer transmit coil 420 and the wireless power transfer receive coil 430. The controller 440 may also be configured to determine a power state of the implantable device (e.g., whether the implantable device needs power). Based on such a determination, the controller 440 may cause a power request to be transmitted to the transmit coil 420 and/or the computing device 410.

The controller 440 may also be used to determine an operating state of a communication system associated with the implantable device. For example, the controller 440 may utilize a communication channel (e.g., a Bluetooth communication channel, an infrared communication channel) to communicate with the computing device 410. If a problem with the communication channel were to arise, the controller 440 could detect the issue.

In response to the detected issue with the communication channel, the controller 440 may cause a telemetry control signal (e.g., a step voltage, ramp voltage) to be applied to the receive coil 430. In an example, the telemetry control signal may range from approximately 0.5 volts to approximately 5 volts although other voltages may be used. The telemetry control signal generates or otherwise causes the wireless power receive coil 430 to provide an inductive telemetry communication signal (e.g., in the form of a waveform) to the wireless power transmit coil 420. The inductive telemetry communication signal may include information about the operating state of the implantable device, an operating state of the communication channel, a request for power, and the like.

As discussed above, the controller 440 may be configured to determine an operating state of the implantable medical device, a power state of the implantable medical device and/or whether power is currently being transferred between the wireless power transmit coil 420 and the wireless power receive coil 430. In some examples, the inductive telemetry communication signal is only generated and/or communicated when a power transfer between the wireless power transmit coil 420 and the wireless power receive coil 430 is not occurring.

In another example, the controller 440 may determine or discover a frequency associated with the power transfer between the wireless power transmit coil 420 and the wireless power receive coil 430 and, subsequently determine a harmonic of that frequency. In such an example, the inductive telemetry communication signal may be provided between the wireless power transmit coil 420 and the wireless power receive coil 430 at the determined harmonic frequency simultaneously or substantially simultaneously with the power transfer. For example, if the frequency for the wireless power transfer is 3.3 megahertz, the inductive telemetry communication signal may be provided at a frequency of 6.6 megahertz.

Although the examples above describe the generation and transmission of inductive telemetry communication signals being a failsafe or backup communication pathway for an existing communication channel, in some examples, the generation and transmission of the inductive telemetry communication signals may be the primary source of communication between the wireless power transmit coil 420 and the wireless power receive coil 430. Additionally, although the examples herein describe the wireless power receive coil 430 as generating and/or transmitting the inductive telemetry communication signal, a telemetry control signal may be applied to the wireless power transmit coil 420. As such, the wireless power transmit coil 420 may generate and/or transmit an inductive telemetry communication signal to the wireless power receive coil 430. Thus, examples of the present disclosure enable bi-directional communication between the wireless power transmit coil 420 and the wireless power receive coil 430.

Figure 5:
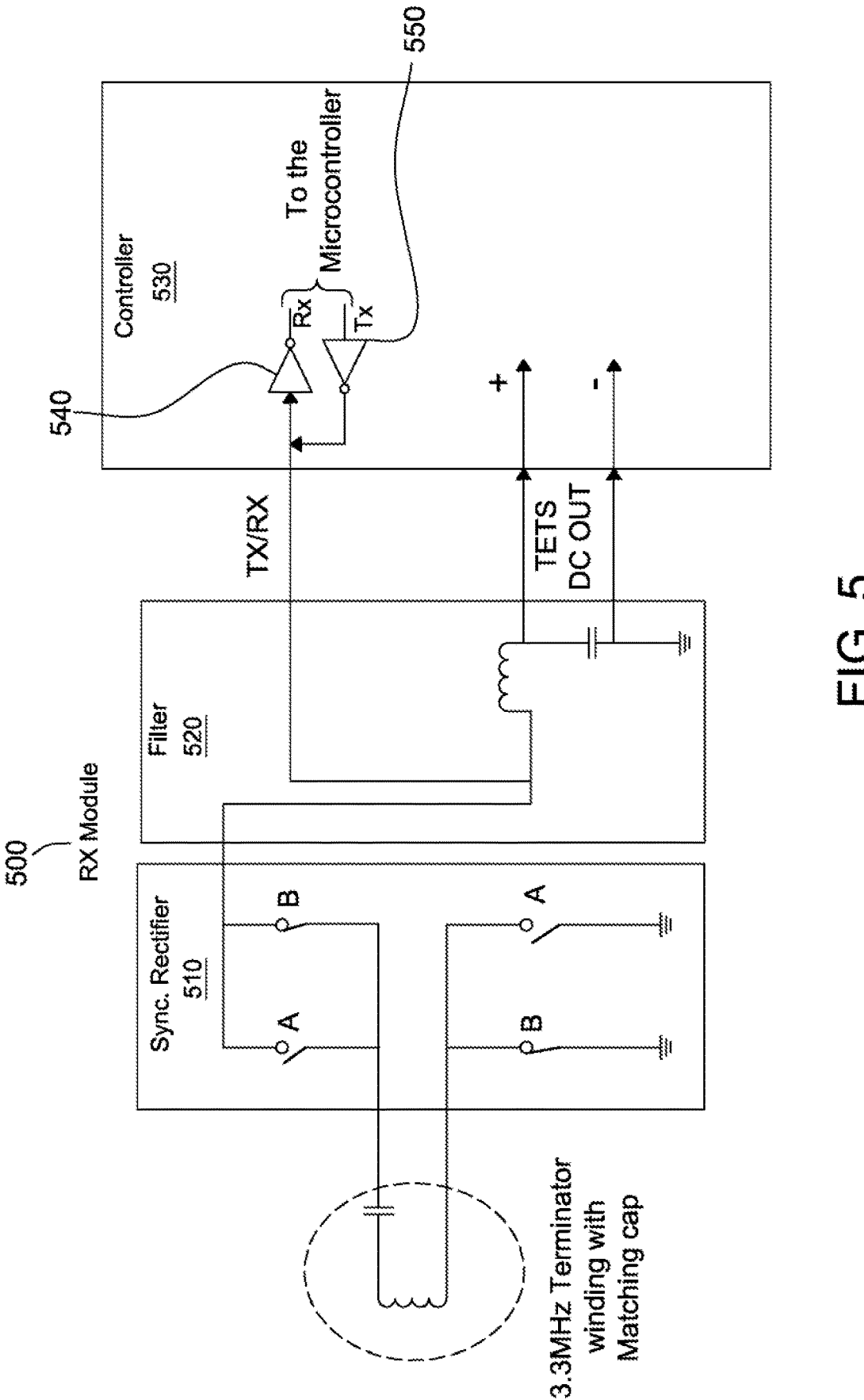
FIG. 5 is a circuit diagram of a wireless power receive coil and an associated controller according to an example.
Figure 6:
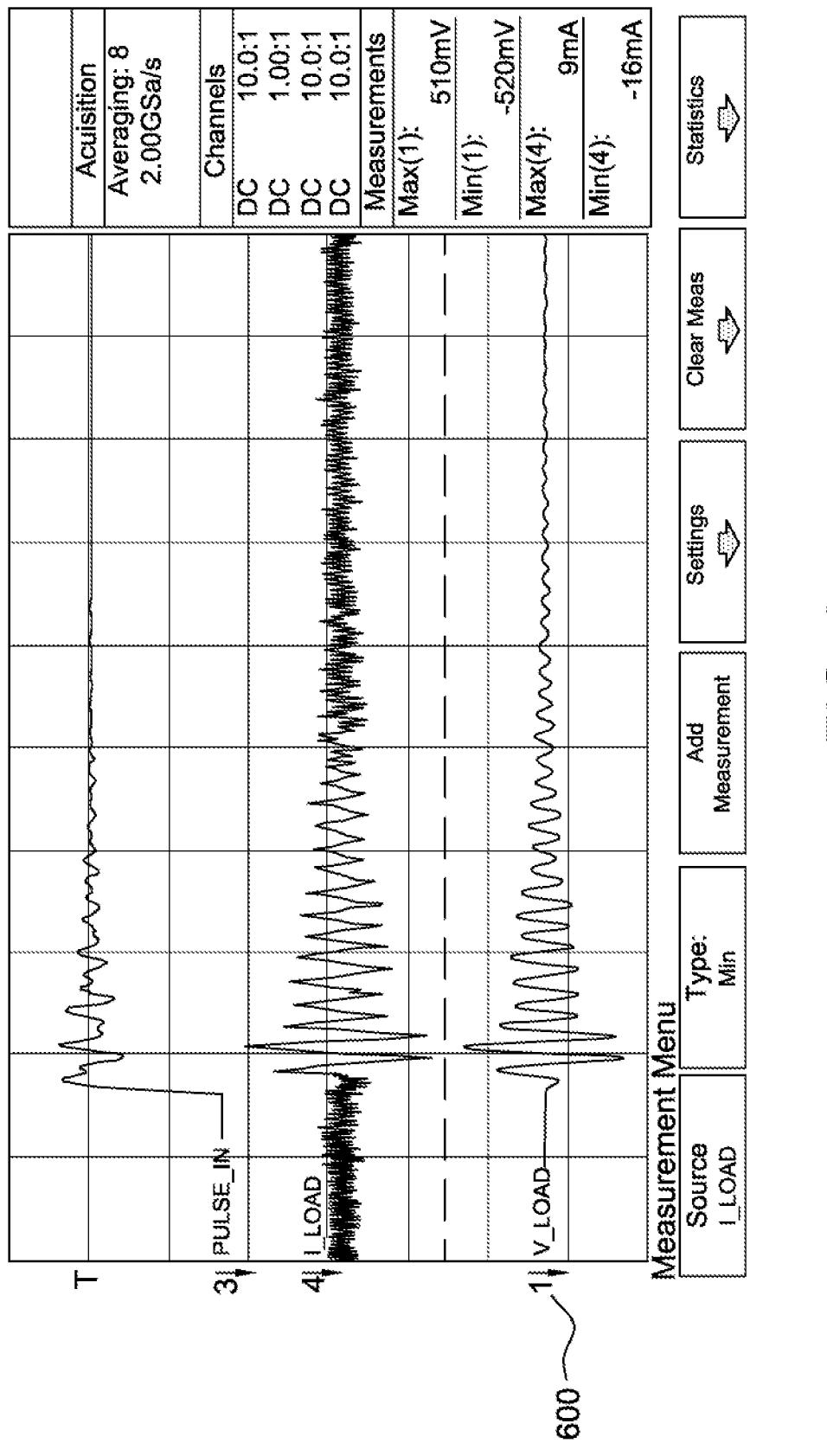
FIG. 6 is an example waveform that may be generated as a result of a telemetry control signal being applied to a wireless power transmit coil or a wireless power receive coil according to an example.

FIG. 5 is a circuit diagram of a wireless power receive coil 500 and an associated controller 530 according to an example. The wireless power receive coil 500 and the controller may be similar to the wireless power receive coil 430 and the controller 440 described above with respect to FIG. 4.

As shown in FIG. 5, the wireless power receive coil 500 may include a synchronization rectifier 510 and a filter 520. The filter 520 may be used to reject, modify and/or reshape unwanted frequencies and/or accept/pass various signals. The synchronization rectifier 510 may be used to convert an alternating current (AC) to a direct current (DC).

The controller 520 may include transmit circuitry 550 and receive circuitry 540. This circuitry allows the controller 520 to cause the wireless power receive coil 500 to switch between a wireless power transfer process and the receipt/generation/transmission of an inductive telemetry communication signal such as described above. For example, when the controller 530 determines that a message or other information is to be provided to a remote computing device, the controller 530 causes a telemetry control signal to be applied to the transmit circuitry 550. The telemetry control signal is converted to a waveform (e.g., waveform 600 (FIG. 6)) and transmitted by the wireless power receive coil 500 to a remote wireless power transmit coil (e.g., wireless power transmit coil 420). Once the waveform is received by the wireless power transmit coil, a computing device associated with the wireless power transmit coil may process the waveform and determine information (e.g., status information of the implantable medical device, a request for power) associated with the waveform.

As discussed above, the step function may cause a frequency of the waveform to be a harmonic of the resonant frequency associated with a wireless power transfer process. Thus, bi-directional communication between the wireless power receive coil 500 and the wireless power transmit coil may occur simultaneously or substantially simultaneously with the power transfer. In another example, the bi-directional communication may occur when a power transfer is not occurring.

Figure 7:
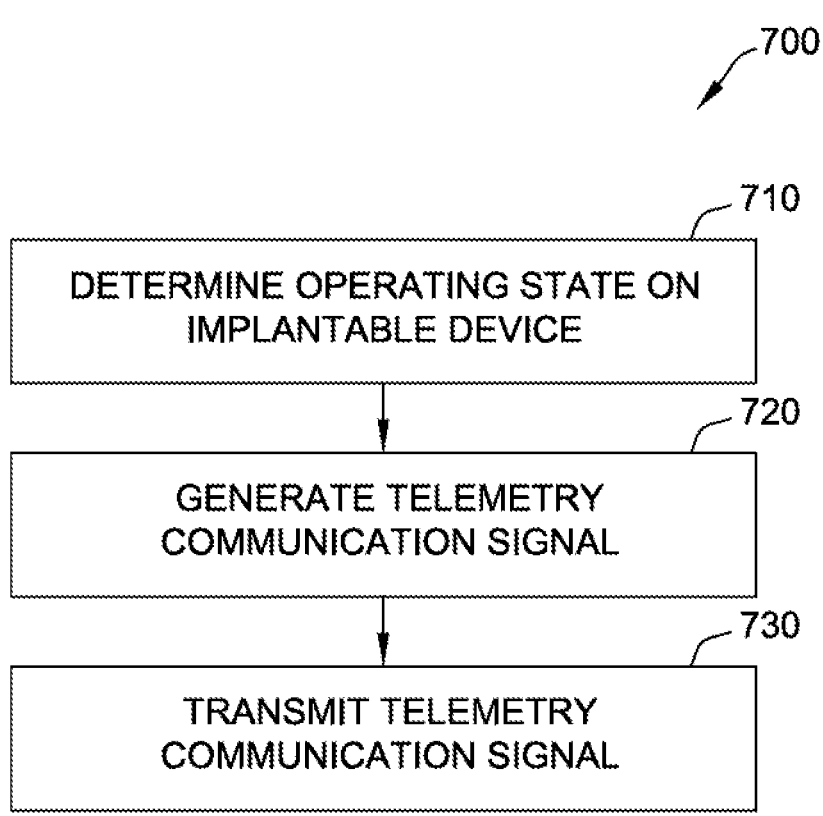
FIG. 7 illustrates a method for generating an inductive telemetry communication according to an example.

FIG. 7 illustrates a method 700 for generating an inductive telemetry communication according to an example. The method 700 may be used by the various components and systems described above.

Method 700 begins when an operating state of an implantable medical device is detected (710). In an example, the operating state of the implantable medical device may be detected by a controller or a computing device communicatively coupled to the implantable medical device.

The operating state of the implantable medical device may include, but is not limited to, determining a power state of the implantable medical device, determining a power transfer state of coils associated with the implantable medical device, determining a status of a communication system and/or channel associated with the implantable medical device and so on.

In response to the determination of the operating state, a controller associated with the implantable medical device may cause a telemetry control signal to be applied (720) to transmit circuitry associated with the controller. The transmit circuitry may provide the telemetry control signal to a wireless power receive coil associated with the controller. The wireless power receive coil may then generate and/or transmit (730) a waveform associated with the telemetry control signal to a wireless power transmit coil. Once the waveform is received, the waveform may be processed by a computing device associated with the wireless power transmit coil.

Although method 700 is described in view of the wireless power receive coil, a wireless power transmit coil may function in a similar manner. Thus, bi-directional communication may occur between a wireless power transmit coil and a wireless power receive coil.

Figure 8:
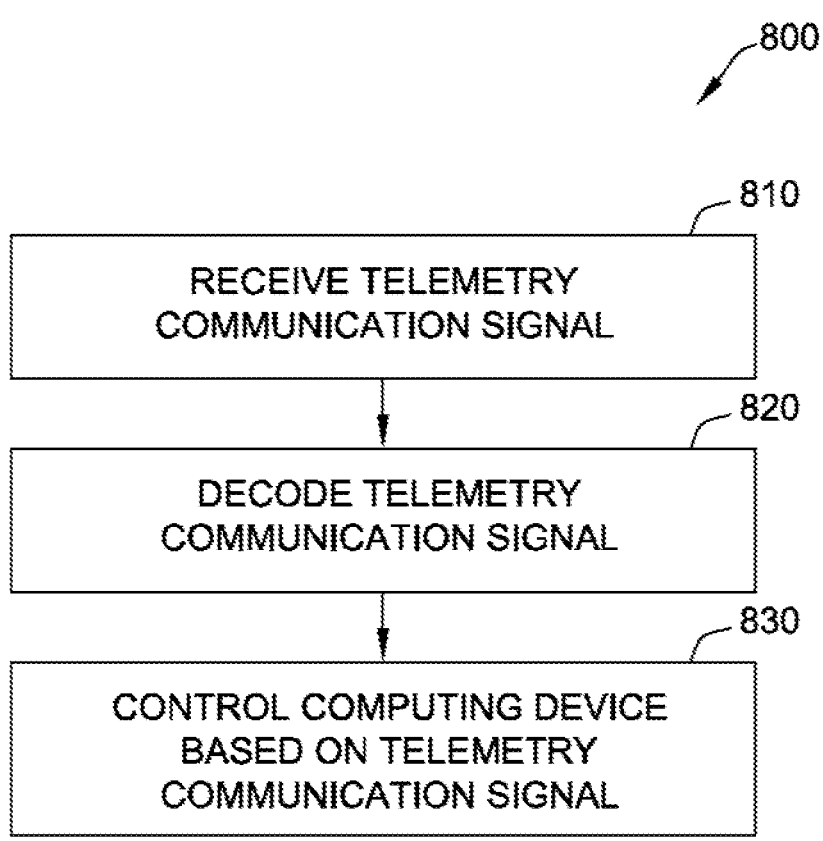
FIG. 8 illustrates a method for receiving and decoding an inductive telemetry communication according to an example.

FIG. 8 illustrates a method 800 for receiving and decoding an inductive telemetry communication according to an example. The method 800 may be used by the various components and systems described above. In some example, the method 800 may be performed in response to the method 700, shown and described with respect FIG. 7, being performed.

Method 800 begins when a telemetry communication signal is received (810). In an example, the telemetry communication signal is received by a wireless power transmit coil from a wireless power receive coil. However, the reverse is also true. That is a wireless power receive coil may receive the telemetry communication signal from a wireless power transmit coil.

When the telemetry communication signal is received, a controller, a computing device, or other processing circuitry associated with the coil that receives the telemetry communication signal, decodes (820) the telemetry communication signal using, for example, a decoder, a comparator and the like.

Once the telemetry communication signal has been decoded, the decoded telemetry communication signal may be used to control (830) the computing device and/or the controller. For example, the decoded telemetry communication signal may include instructions for the computing device or the controller. In another example, the decoded telemetry communication signal may include information about the implantable device. As the information is received, the computing device or the controller may analyze the information and take an action based, at least in part, on the information.

Although the examples disclosed herein have been described with reference to particular figures, it is to be understood that these examples are merely illustrative of the principles and applications of the present disclosure. It is therefore to be understood that numerous modifications can be made to the illustrative examples and that other arrangements can be devised without departing from the spirit and scope of the present disclosure as defined by the claims. Thus, it is intended that the present application cover the modifications and variations of these examples and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:

providing a telemetry control signal to a transmit circuitry of a controller associated with a transcutaneous energy transfer system for an implantable device, wherein the telemetry control signal is a voltage;

generating the telemetry control signal to a wireless power transfer receive coil of the transcutaneous energy transfer system to induce a resonant voltage in the wireless power transfer receive coil, wherein the induced resonant voltage generates an inductive telemetry communication signal; and transmitting the inductive telemetry communication signal from the wireless power transfer receive coil to a wireless power transfer transmit coil of the transcutaneous energy transfer system, wherein power is transferred between the wireless power transfer transmit coil and the wireless power transfer receive coil at a frequency, and wherein the inductive telemetry communication signal is transmitted from the wireless power transfer receive coil to the wireless power transfer transmit coil at a harmonic of the frequency.

2. The method of claim 1, further comprising detecting an operating state of the transcutaneous energy transfer system.

3. The method of claim 2, further comprising providing the telemetry control signal to the transmit circuitry of the controller based, at least in part, on the operating state of the transcutaneous energy transfer system.

4. The method of claim 1, wherein the telemetry control signal is in a range between 0.5 volts to 5 volts.

5. The method of claim 1, wherein the controller is associated with the implantable device.

6. The method of claim 5, wherein the telemetry control signal is provided to the transmit circuitry of the controller based, at least in part, on a detected operating state of the implantable device.

7. The method of claim 5, wherein the telemetry control signal is provided to the transmit circuitry of the controller based, at least in part, on a detected operating state of a communication system associated with the implantable device.

8. The method of claim 1, wherein said providing the telemetry control signal to the transmit circuitry includes the telemetry control signal being selected from a group consisting of a step voltage, a ramp voltage, and a piecewise linear edge voltage.

9. The method of claim 1, wherein said transmitting the inductive telemetry communication signal from the wireless power transfer receive coil to the wireless power transfer transmit coil includes the inductive telemetry communication signal being a bi-directional inductive telemetry communication signal.

10. A transcutaneous energy transfer system for an implantable device, comprising:
a wireless power transfer transmit coil;
a wireless power transfer receive coil; and
a controller associated with the wireless power transfer receive coil, the controller associated with the transcutaneous energy transfer system including a transmit circuitry and a receive circuitry, the controller configured to
generate a telemetry control signal to the wireless power transfer receive coil to induce a resonant voltage in the wireless power transfer receive coil, wherein the telemetry control signal is a voltage, the induced resonant voltage generating an inductive telemetry communication signal; and
transmit the inductive telemetry communication signal from the wireless power transfer receive coil to the wireless power transfer transmit coil, wherein power is transferred between the wireless power transfer transmit coil and the wireless power transfer receive coil at a frequency, and wherein the inductive telemetry communication signal is transmitted from the wireless power transfer receive coil to the wireless power transfer transmit coil at a harmonic of the frequency.

11. The transcutaneous energy transfer system of claim 10, wherein the telemetry control signal is in a range between 0.5 volts to 5 volts.

12. The transcutaneous energy transfer system of claim 10, wherein the controller detects an operating state of the transcutaneous energy transfer system.

13. The transcutaneous energy transfer system of claim 10 further comprising a processing system associated with the wireless power transfer transmit coil for processing the inductive telemetry communication signal.

14. The transcutaneous energy transfer system of claim 10 wherein the wireless power transfer transmit coil is configured to transmit a second inductive telemetry communication signal to the wireless power transfer receive coil in response to a second telemetry control signal being received by the controller associated with the wireless power transfer transmit coil.

15. The transcutaneous energy transfer system of claim 10, wherein the controller is further configured to generate the telemetry control signal to the wireless power transfer receive coil to induce the resonant voltage in the wireless power transfer receive coil, wherein the telemetry control signal is selected from a group consisting of a step voltage, a ramp voltage, and a piecewise linear edge voltage.

16. A method, comprising:
detecting an operating state of a communication system associated with an implantable device, the implantable device having a transcutaneous energy transfer system, the transcutaneous energy transfer system including a wireless power transfer transmit coil and a wireless power transfer receive coil;
in response to detecting the operating state of the communication system, providing a telemetry control signal to a transmit circuitry of a controller associated with the transcutaneous energy transfer system, wherein the telemetry control signal is a voltage;
generating the telemetry control signal to the wireless power transfer receive coil to induce a resonant voltage in the wireless power transfer receive coil, wherein the induced resonant voltage generates an inductive telemetry communication signal; and
transmitting the inductive telemetry communication signal from the wireless power transfer receive coil to the wireless power transfer transmit coil, wherein power is transferred between the wireless power transfer transmit coil and the wireless power transfer receive coil at a frequency, and wherein the inductive telemetry communication signal is transmitted from the wireless power transfer receive coil to the wireless power transfer transmit coil at a harmonic of the frequency.

17. The method of claim 16, wherein the telemetry control signal is in a range between 0.5 volts to 5 volts.

18. The method of claim 16, wherein the telemetry control signal is provided to the transmit circuitry of the controller based, at least in part, on a detected operating state of the implantable device.

19. The method of claim 16, further comprising providing the inductive telemetry communication signal to a processing system associated with the implantable device.

20. The method of claim 16, further comprising causing a wireless transfer of the power between the wireless power transfer transmit coil and the wireless power transfer receive coil to cease when the inductive telemetry communication signal is transmitted from the wireless power transfer receive coil to the wireless power transfer transmit coil.

* * * * *